United States Patent
Yamaura et al.

(10) Patent No.: US 8,987,383 B2
(45) Date of Patent: Mar. 24, 2015

(54) TRIAZINE DERIVATIVES AND APPLICATION THEREOF

(75) Inventors: Mabuko Yamaura, Fukushima-ken (JP);
Yukio Orikasa, Fukushima-ken (JP);
Kazuya Senzaki, Fukushima-ken (JP);
Takashi Kagawa, Fukushima-ken (JP)

(73) Assignee: Nippon Kasei Chemical Company Limited, Iwaki (JP)

( * ) Notice: Subject to any disclaimer, the term of this patent is extended or adjusted under 35 U.S.C. 154(b) by 295 days.

(21) Appl. No.: 13/579,376

(22) PCT Filed: Feb. 3, 2011

(86) PCT No.: PCT/JP2011/052249
§ 371 (c)(1),
(2), (4) Date: Sep. 28, 2012

(87) PCT Pub. No.: WO2011/102231
PCT Pub. Date: Aug. 25, 2011

(65) Prior Publication Data
US 2013/0023629 A1   Jan. 24, 2013

(30) Foreign Application Priority Data
Feb. 17, 2010  (JP) ............................... 2010-032467

(51) Int. Cl.
| | | |
|---|---|---|
| C07D 251/46 | (2006.01) | |
| C07D 251/26 | (2006.01) | |
| C07D 251/52 | (2006.01) | |
| C08K 5/3492 | (2006.01) | |
| C08C 19/22 | (2006.01) | |
| C07D 251/40 | (2006.01) | |
| C08C 19/28 | (2006.01) | |
| C07D 251/70 | (2006.01) | |
| C07D 251/30 | (2006.01) | |
| C08K 5/00 | (2006.01) | |
| C08L 23/08 | (2006.01) | |

(52) U.S. Cl.
CPC .......... C07D 251/46 (2013.01); *C08F 2810/20* (2013.01); C07D 251/26 (2013.01); *C08C 19/22* (2013.01); *C07D 251/40* (2013.01); *C08C 19/28* (2013.01); *C07D 251/70* (2013.01); *C07D 251/30* (2013.01); C07D 251/52 (2013.01); *C08K 5/0025* (2013.01); C08K 5/3492 (2013.01); *C08L 23/0853* (2013.01); *C08L 2312/00* (2013.01)
USPC .................... 525/281; 525/326.2; 525/330.5; 525/375; 544/196

(58) Field of Classification Search
None
See application file for complete search history.

(56) References Cited

U.S. PATENT DOCUMENTS

| | | | | |
|---|---|---|---|---|
| 2,537,816 A | * | 1/1951 | Dudley et al. | 544/219 |
| 3,306,725 A | * | 2/1967 | Enrico Knusli et al. | 504/232 |
| 4,116,914 A | * | 9/1978 | Coran et al. | 525/222 |
| 4,460,748 A | | 7/1984 | Rauer | |

FOREIGN PATENT DOCUMENTS

| | | |
|---|---|---|
| DE | 1 064 071 | 8/1959 |
| DE | 2308560 | * 9/1974 |
| DE | 2506105 | 8/1976 |
| JP | 54-038342 | 3/1979 |
| JP | 06-206955 | 7/1994 |
| JP | 2003-238761 | 8/2003 |
| JP | 2006-273995 | 10/2006 |
| JP | 2009-057501 | 3/2009 |
| WO | WO 2009/139141 | 11/2009 |

OTHER PUBLICATIONS

Computer Translation of DE 2308560 (1974).*
V. D. Vorotyntseva et al., Infrared Spectra and Raman Spectra of S-Triazine Derivatives with Amino, Alkoxy, and Alklamino Type Substitutes, 1972, vol. 17, No. 2, pp. 286-289, Chemical abstracts, vol. 77, 1972, p. 417, abstract No. 145872, pp. 287-288, tables 1-2.
H. Anne, et al., Partial Aminolysis of 2, 4, 6-Triallyloxy-s-triazine. I. Preparation of 2-alkyl (˜en) amino-4,6-diallyloxy-triazines, Synthesis, 1975, No. 3, pp. 182-184, Chemical abstracts, vol. 82, 1975, p. 603, abstract No. 156228, compounds 1, 2c.

(Continued)

Primary Examiner — Robert C Boyle
(74) Attorney, Agent, or Firm — Nixon & Vanderhye P.C.

(57) ABSTRACT

The object of the present invention is to provide a novel triazine derivative which is excellent in the heat resistance and rapid in the cross-linking rate, and can be suitably used as a crosslinking agent.

The present invention relates to a triazine derivative represented by the general formula (I).

[Chemical formula 1]

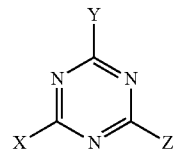

(I)

(In the formula (I), Y and X are each independently, represents a diallylamino group, mono-allylamino group, allyloxy group or methallyloxy group; and Z represents an allyloxy group or methallyloxy group).

15 Claims, No Drawings

(56) References Cited

OTHER PUBLICATIONS

K. Seta et al., "Kobunshi Hashikakezai to Shite no Fuhowa Cyanurate-gata Novolac", The Journal of Chemical Industry, 1968, vol. 70, No. 5, pp. 784-788, Chemical abstracts, vol. 68, 1968, p. 4901, abstract No. 50432.

V.D. Vorotyntseva et al., Infrared Spectra and Raman Spectra of S-Triazine Derivatives with Amino, Alkoxy, and Alklamino Type Substitutes, 1972, vol. 17, No. 2, pp. 286-289, Chemical abstracts, vol. 77, 1972, p. 417, abstract No. 145872, pp. 287-288, tables 1-2.

Extended European Search Report in EP 11 74 4519.7 dated May 13, 2013.

* cited by examiner

TRIAZINE DERIVATIVES AND APPLICATION THEREOF

This application is the U.S. national phase of International Application No. PCT/JP2011/052249 filed 3 Feb. 2011 which designated the U.S. and claims priority to JP 2010-032467 filed 17 Feb. 2010, the entire contents of each of which are hereby incorporated by reference.

TECHNICAL FIELD

The present invention relates to a triazine derivative and applications thereof. More specifically, the present invention relates to a triazine derivatives and application thereof having a novel structure. In the present invention, the term of cross-linkable polymer means both a cross-linkable elastomer and a cross-linkable thermoplastic.

BACKGROUND ART

Isocyanurate derivatives, especially triallyl isocyanurate (hereinafter referred as TRIC) is known as a cross-linking agent useful in obtaining a molded product by curing the cross-linkable polymer.

However, although the cross-linkable polymer molded product using TAIC is excellent in the chemical resistance and compression permanent strain, the heat resistance is insufficient. Also, if TAIC is used for a substituted polyolefin, especially an ethylene-vinyl acetate copolymer, there is a disadvantage that the time of cross-linking process becomes longer because of slow cross-linking rate.

On the other hand, it is known that triazine derivatives such as tris(diallylamino)-s-triazine is used as the crosslinking agent (Patent Document 1), the triazine derivative having has excellent heat resistance compared to TAIC (Patent Document 1).

PRIOR DOCUMENTS

Patent Documents

Patent Document 1: Japanese Patent Application Laid-Open (KOHYO) No. 2005-433162

SUMMARY OF THE INVENTION

Problems to be Solved by the Invention

The object of the present invention is to provide a novel triazine derivative which is excellent in the heat resistance and rapid in the cross-linking rate in comparison with TAIC, and can be suitably used as a crosslinking agent.

Means for Solving the Problems

Thus, in a first aspect of the present invention, there is provided a triazine derivative represented by the general formula (I).

[Chemical formula 1]

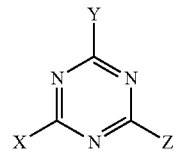

(I)

(In the formula (I), Y and X are each independently, represents a diallylamino group, mono-allylamino group, allyloxy group or methallyloxy group; and Z represents an allyloxy group or methallyloxy group)

In a second aspect of the present invention, there is provided a cross-linking agent comprising the triazine derivative represented by the above general formula (I) or prepolymer thereof In a third aspect of the present invention, there is provided a cross-linkable polymer composition comprising a cross-linkable polymer and the triazine derivative represented by the above general formula (I) or prepolymer thereof blended thereto, the blending ratio of triazine derivative or prepolymer thereof being 0.05 to 15 parts by weight based on 100 parts by weight of cross-linkable polymer.

In a fourth aspect of the present invention, there is provided a process for producing a polymer molded product by curing a cross-linkable polymer, which process comprising using the triazine derivative represented by the above general formula (I) or prepolymer thereof.

In a fifth aspect of the present invention, there is provided a polymer molded product cured by the action of a crosslinking agent, produced by using the triazine derivative represented by the above general formula (I) or prepolymer thereof as a cross-linking agent.

Effect of the Invention

According to the present invention, there is provided a novel triazine derivative which is excellent in the heat resistance and rapid in the cross-linking rate in comparison with TAIC, and can be suitably used as a crosslinking agent.

BEST MODE FOR CARRYING OUT THE INVENTION

The present invention will be described in detail below.
<Triazine Derivative>
The triazine derivative according to the present invention is represented by the general formula (I).

[Chemical formula 2]

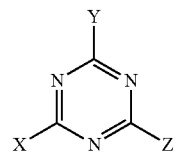

(I)

(In the formula (I), Y and X are each independently, represents a diallylamino group, mono-allylamino group, allyloxy group or methallyloxy group; and Z represents an allyloxy group or methallyloxy group)

Specific examples of the triazine derivative represented by the general formula (I) include 4,6-bis(diallylamino)-2-allyloxy-1,3,5-triazine, 4,6-bis(allylamino)-2-allyloxy-1,3,5-triazine, 4,6-bis(allyl-methylamino)-2-allyloxy-1,3,5-triazine, 4,6-bis(diallylamino)-2-methallyloxy-1,3,5-triazine, 4,6-bis(allylamino)-2-methallyloxy-1,3,5-triazine, 4,6-bis(allyl-methylamino)-2-methallyloxy-1,3,5-triazine, 4,6-bis(allyloxy)-2-diallylamino-1,3,5-triazine, 4,6-bis(allyloxy)-2-allylamino-1,3,5-triazine, 4,6-bis(allyloxy)-2-(allyl-methylamino)-1,3,5-triazine, 4,6-bis(methallyloxy)-2-diallylamino-1,3,5-triazine, 4,6-bis(methallyloxy)-2-allylamino-1,3,5-triazine, 4,6-bis(methallyloxy)-2-(allyl-methylamino)-1,3,5-triazine, 2-allyloxy-4-allylamino-6-diallylamino-1,3,5-triazine, 2-allyloxy-4-(allyl-methylamino)-6-diallylamino-1,3,5-triazine, 2-allyloxy-4-(allyl-methylamino)-6-allylamino-1,3,5-triazine, 2-methallyloxy-4-allylamino-6-diallylamino-1,3,5-triazine, 2-methallyloxy-4-(allyl-methylamino)-6-diallylamino-1,3,5-triazine, 2-methallyloxy-4-(allyl-methylamino)-6-allylamino-1,3,5-triazine or the like.

The triazine derivative represented by the general formula (I) can be easily obtained by such a method that for example, cyanuric chloride is reacted with diallylamine or mono-allyl amine in the presence of a base and the obtained reaction product is further reacted with allyl alcohol. As the base, there are exemplified alkali metal carbonate such as potassium carbonate and sodium carbonate, alkali metal hydroxides such as sodium hydroxide and potassium hydroxide. There is a case where a tertiary amine such as triethylamine or an amine as the reaction component is used as the base. As the reaction solvent, there may be used tetrahydrofuran (THF), dioxane, toluene, N,N-dimethylformamide, N,N-dimethylacetamide or the like. The reaction temperature may vary depending on the type of reaction components, and is generally about 20 to 200° C. The identification analysis of the obtained compound can be carried out by NMR spectroscopy, GC-MS analysis, HPLC analysis and measurement of melting point.

<Cross-Linking Agent>

The cross-linking agent according to the present invention comprises a triazine derivative represented by the above general formula (I) or prepolymer thereof.

The above triazine derivatives and prepolymer thereof can be obtained by radical-polymerizing the monomer with an organic peroxide or the like as an initiator. The number-average molecular weight thereof is usually 1000 to 20000, preferably 2000 to 7000.

The above triazine derivative and prepolymer thereof is used as the cross-linking agent and the types and usage of objective cross-linkable polymer will be described in the later description for the other invention.

<Cross-Linkable Polymer Composition>

The cross-linkable polymer composition according to the present invention is prepared by blending at least the triazine derivative represented by the above general formula (I) or prepolymer thereof into the cross-linkable polymer. The blending amount of triazine derivative or prepolymer thereof is 0.05 to 15 parts by weight based on 100 parts by weight of cross-linkable polymer.

The cross-linkable polymer used in the present invention is a cross-linkable elastomer or a cross-linkable thermoplastic resin.

The cross-linkable elastomer means an elastomer having an active site which can be cross-linked by radical generation. The kind of cross-linkable elastomer is not particularly limited, for example, natural rubber, isoprene rubber, butadiene rubber, ethylene propylene rubber, styrene rubber, nitrile rubber, hydrogenated nitrile rubber, chloroprene rubber, chlorosulfonated polyethylene, acrylic rubber, ethylene acrylic rubber, silicone rubber, fluorine rubber, hydrin rubber or the like may be mentioned. In addition, there are exemplified substituted olefins which is a copolymer of olefin such as ethylene and propylene with vinyl alcohol, acrylic acid, methacrylic acid, ethyl acrylate, glycidyl methacrylate, vinyl acetate or the like. Further, a blended rubber comprising two or more components mentioned above may be also used. Of these, the fluorine rubber is preferred. The type of fluorine rubber is not particularly limited, FKM-based rubber, FFKM-based rubber, FEPM-based rubber, TFE-based rubber or the like may be mentioned. Of these, preferred thereof are the substituted olefins such as ethylene-vinyl acetate copolymer or fluorine rubbers. The vinyl acetate content in the ethylene-vinyl acetate copolymer is usually 10 to 40% by weight, preferably 20 to 35% by weight.

The cross-linkable thermoplastic resin means a thermoplastic resin having an active site which can be cross-linked by radical generation. The kind of cross-linkable thermoplastic resin is not particularly limited, for example, a vinyl chloride resin, polyolefin resin, acrylic resin, polystyrene resin, polycarbonate resin, polyester resin, polyamide resin, polyphenylene ether resin, polyacetal resin, fluorine resin or the like may be mentioned. A blend of two or more resins of these may be used. Of these, a polyamide resin and polyester resin are preferred, polyamide 6, polyamide 66 and polybutylene terephthalate are more preferred.

The blending ratio of triazine derivative or prepolymer thereof to the cross-linkable polymer is preferably 0.05 to 15% by weight.

In the present invention, the other cross-linking agent may be used in combination with the above-mentioned cross-linking agent. The other cross-linking agents include, but are not particularly limited, an isocyanurate derivative represented by the following general formula (II) is preferred.

[Chemical formula 3]

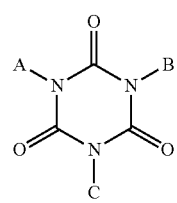

(II)

(In the formula (II), at least two of A, B, and C each independently represent an allyl group which may be substituted, and the rest represents a hydrogen atom or a hydrocarbon group which may be substituted.)

As the hydrocarbon group, there are exemplified an aliphatic hydrocarbon group, an aromatic hydrocarbon group and the alicyclic hydrocarbon group which have 1 to 10 carbon atoms. Aliphatic hydrocarbon group also may have a branched structure which may have a substituent. As specific examples of the hydrocarbon group, there are exemplified an alkyl group, alkenyl group, an alkoxy group, a thioalkyl group, an alkoxycarbonyl group, a cyclohexyl group, phenyl group, benzyl group or the like. In addition, A, B and C in the formula (II) may be the same or different each other.

The isocyanurate derivative represented by the general formula (II) has been already known. As specific examples thereof, there are exemplified triallyl isocyanurate (TAIC), diallylmethallyl isocyanurate, diallylbenzyl isocyanurate, diallyl-4-trifluoromethylbenzyl isocyanurate, tri-methallyl isocyanurate, diallylmethyl isocyanate, ethoxycarbonyl methyldiallyl isocyanate or the like.

When using the triazine derivative or prepolymer thereof and the above isocyanurate derivative in combination, the total amount thereof is usually 0.05 to 15 parts by weight, preferably from 0.5 to 5 parts by weight based on 100 parts by weight of the cross-linkable polymer. The percentage of isocyanurate derivative to the total of all cross-linking agent is usually 5 to 95% by weight.

Further, in addition to the above isocyanurate derivative, polyfunctional (meth)acrylate may be used in combination. The polyfunctional (meth)acrylate has two or more, preferably three or more (meth)acryloyl groups in one molecule. More specifically, there are exemplified trimethylolpropane tri(meth)acrylate, pentaerythritol tri(meth)acrylate, tris ((meth)acryloxyethyl) isocyanurate, dimethylolpropane tetra (meth)acrylate, tetraethylene glycol di(meth)acrylate, nonaethylene glycol di(meth)acrylate or the like. The amount of these polyfunctional (meth)acrylate added is 0.05 to 15 parts by weight based on 100 parts by weight of cross-linkable polymer.

To the cross-linkable polymer composition, an organic peroxide may be blended. The organic peroxide is usually an essential component for the heat cross-linking, and is not particularly limited as long as it is a known organic peroxide to generate peroxy radicals under the vulcanization conditions. There are exemplified di-t-butylperoxide, dicumylperoxide, 2,5-dimethyl-2,5-di(benzoylperoxy) hexane, 2,5-dimethyl-2,5-di(t-butylperoxy) hexane, t-butylperoxy-2-ethylhexyl-monocarbonate, 1,1-bis(t-butylperoxy)-3,5,5-trimethyl cyclohexane, 2,5-dimethyl-2,5-dihydroxyperoxide, t-butylcumylperoxide, α,α'-bis(t-butylperoxy)-p-diisopropyl benzene, 2,5-dimethyl-2,5-di(t-butylperoxy) hexyne, benzoylperoxide, t-butylperoxy benzene or the like.

The blending amount of the organic peroxide, may vary depending on the type of used cross-linkable polymer, and is usually 0.1 to 10% by weight, preferably 0.5 to 5% by weight based on 100 parts by weight of the cross-linkable polymer. In case of radiation cross-linking, the organic peroxide is not necessarily required.

In the present invention, known additives such as a polymerization inhibitor, filler, pigment, stabilizer, lubricant, releasing agent, plasticizer, anti-aging agent, silane coupling agent, ultraviolet absorber, flame retardant and acid acceptor can be used.

As the anti-aging agent, there are exemplified di-t-butyl-P-cresol, pentaerythrityl-tetraxy[3-(3,5-di-t-butyl-4-hydroxyphenyl)propionate], 2,2'-methylenebis(2-methyl-6-t-butylphenyl), bis(2,2,6,6-tetramethyl-4-piperadyl)sebacate, N,N'-hexane-1,6-diylbis[3-(3,5-di-tert-butyl-4-hydroxyphenyl)propionamido], bis(2,2,6,6-tetramethyl-4-piperadyl)sebacate, hydroquinone monomethylether, methylhydroquinone or the like.

As the silane coupling agent, there are exemplified γ-chloropropyl trimethoxysilane, vinyl triethoxysilane, vinyl-tris-(β-methoxyethoxy) silane, γ-methacryloxypropyl trimethoxysilane, β-(3,4-ethoxy-cyclohexyl)ethyl trimethoxysilane, γ-glycidoxypropyl trimethoxysilane, γ-mercaptopropyltrimethoxysilane, γ-aminopropyl trimethoxysilane, N-β-(aminoethyl)-γ-aminopropyl trimethoxysilane or the like.

As the ultraviolet absorber, there are exemplified 2-hydroxy-4-n-octyloxy benzophenone, 2,2-hydroxy-4,4-dimethoxy benzophenone, 2-(2'-hydroxy-5-methylphenyl) benzotriazole, p-t-butylphenyl salicylate or the like.

The blending amount of the above additive is usually not more than 10 parts by weight, preferably 5 parts by weight based on 100 parts by weight of the cross-linkable polymer.

Each of the above ingredients are mixed by a usual kneader such as a Banbury mixer, a kneader, an open roll or the like to form a cross-linkable polymer composition.

<Process for Producing an Polymer Molded Product>

The process according to the present invention is a process for producing an polymer molded product by curing the cross-linkable polymer. Then, as the cross-linking agent, the triazine derivative represented by the above general formula (I) or prepolymer thereof is used. As the cross-linking, either heating cross-linking and radiation cross-linking may be used, heating cross-linking is preferred.

The heating cross-linking is conducted by such a manner that, after filling a prescribed amount of cross-linkable polymer composition is filled in a mold having a desired shape, and subjected to primary cross-linking by a heating process, if necessary, secondary cross-linking is applied in the oven. The shape of mold in the molding machine can be optionally selected from, for example, a sheet-shape, rod-shape, ring-shape and various complex block-shapes depending on the application of obtained polymer molded product.

The primary cross-linking is conducted by heating thereof at usually 120 to 200° C. for 2 to 30 minutes by use of, for example, an injection molding machine, pressurizing molding machine or the like.

The secondary cross-linking is conducted at 120 to 300° C. for 1 to 72 hours. Especially, by conducting the secondary cross-linking at 200 to 300° C. for 1 to 72 hours, a polymer molded product having good mechanical strength can be obtained.

In addition, as the radiation used in the radiation cross-linking, there ca be used an electron beam acceleration, X-ray, α-ray, β-ray, γ-ray or the like. The irradiation dose may vary depending on the used cross-linkable elastomer type is usually 0.1 to 500 kGy.

<Polymer Molded Product>

The polymer molded product according to the present invention is an polymer molded product cured by the action of cross-linking agent. As the cross-linking agent, the triazine derivative represented by the above general formula (I) or prepolymer thereof is used. The process for producing thereof is as described above.

Incidentally, although the mechanical properties in polymer molded products are important, it is not necessarily easy to develop the maximum effect of heating cross-linking process. Therefore, when using the heating cross-linking process, usually, it is difficult to produce a polymer molded product which is sufficiently prevented from the degradation of mechanical properties due to the heating.

On the other hand, the polymer molded product according to the present invention is sufficiently prevented from the deterioration of mechanical properties due to the heating. For example, the polymer molded product according to the present invention has such a property that a rate of tensile strength change (MPa) measured according to ASTM D 638 before and after the thermal degradation tests under the following conditions (ratio of the difference of the tensile strengths between after and before the test to the tensile strength before the test) is −55% to 0%.

[Conditions of Thermal Degradation Test]

A test piece (punched out to the form No. 3 dumbbell-shaped as defined JIS K 6251) is used and treated in a gear oven at 250° C. for 70 hours.

The above conditions: "treated in a gear oven at 250° C. for 70 hours" corresponds to the conditions of "accelerated aging test" in a vulcanized rubber as defined in JIS K6257.

As the gear oven, for example, there may be used "Gear heat aging testing machine" (type ACR-60A) manufactured by Toyo Seiki Seisaku-Sho, Ltd., which is commercially available as the accelerated aging test machine for polymeric materials such as rubber, plastic or the like.

EXAMPLES

The present invention is described in more detail below by the following Examples. However, these Examples are only illustrative and not intended to limit the present invention thereto unless they depart from the scope of the present invention.

Synthesis Example 1

Synthesis of 4,6-bis(diallylamino)-2-allyloxy-1,3,5-triazine

After 21.2 g (0.20 mol) of sodium carbonate and 20.0 g (0.10 mol) of cyanuric chloride were added and dissolved into 140 g of 1,4-dioxane, 19.8 g (0.20 mol) of diallylamine was gradually added thereinto and further, 8.4 g (0.20 mol) of caustic soda was added thereinto. By generating the heat of reaction, the temperature of reaction solution was raised to about 60° C. and the reaction was continued at the temperature for 2 hours. Thereafter, the reaction mixture was cooled and filtered to remove the sodium chloride generated as the byproduct. The obtained filtrate was distilled under reduced pressure to recover the solvent. Therefore, 34 g (0.09 mol) of 4,6-bis(diallylamino)-2-chloro-1,3,5-triazine was obtained.

Then, after 3.8 g (0.09 mol) of caustic soda and 34 g (0.09 mol) of the above obtained 4,6-bis(diallylamino)-2-chloro-1,3,5-triazine were added and dissolved into 240 g of 1,4-dioxane, 5.3 g (0.09 mol) of allyl alcohol was gradually added. By generating the heat of reaction, the temperature of reaction solution was raised to about 80° C. and the reaction was continued at the temperature for 8 hours. Thereafter, the reaction mixture was cooled and filtered to remove the sodium chloride generated as the byproduct (forming by reaction of 4,6-bis(diallylamino)-2-chloro-1,3,5-triazine as the reaction material with the caustic soda). The obtained filtrate was distilled under reduced pressure to recover the solvent. The obtained residue was diluted with ethyl acetate, washed with 5% by weight of aqueous hydrochloric acid solution, washed with water and thereafter, dried by anhydrous magnesium sulfate and filtered. The obtained filtrate is distilled under reduced pressure to recover the ethyl acetate contained therein. Further, the residue was distilled (distillation temperature: 155° C., degree of vacuum: 0.5 Torr) to obtain 27.4 g of liquid 4,6-bis(diallylamino)-2-allyloxy-1,3,5-triazine (LC purity: 99%, yield: 80%).

The structure of synthesized triazine derivatives were identified by GC-MS and NMR. The NMR and GC-MS measurements conditions are shown in Tables 1 and 2.

TABLE 1

| (NMR) | |
|---|---|
| Equipment type | Gemini-200 manufactured by Varian, Inc. |
| Nuclide | H-1 |
| Solvent | Chloroform-d |
| Cumulated number | 16 |

TABLE 2

| (GC-MS) | |
|---|---|
| Equipment type | QP-2010 Plus, manufactured by Shimadzu Corporation |
| Column | HP-5, 30 m × 0.32 mm |
| Column temperature | 100° C. to 300° C. Rate of temperature increase: 10° C./min |
| Inlet temperature | 250° C. |
| Ion source temperature | 230° C. |
| Interface temperature | 300° C. |
| Pressure | 100 kPa |
| Split ee | 1:20 |
| Ion source | NCI, SEI, SCI |

The NMR measurement results of the above triazine derivative were δ: 5.7-6.2 ppm, 5H(m), 5.05-5.42 ppm, 10H(m), 4.75 ppm, 2H(d), 4.18 ppm, 8H(b), and GC-MS measurement was (CI)(M+1): 328.

The above "LC purity" was determined as an area percentage by conducting liquid chromatography measurement where an "INERTSIL ODS-3" column (25 cm) was set to "LC-10ADVP" manufactured by Shimadzu Corporation and a mixed solvent of acetonitrile and water was used.

Synthesis Example 2

Synthesis of 4,6-bis(allyloxy)-2-diallylamino-1,3,5-triazine

After 10.6 g (0.10 mol) of sodium carbonate and 20.0 g (0.10 mol) of cyanuric chloride were added and dissolved into 140 g of 1,4-dioxane, 9.9 g (0.10 mol) of diallylamine was gradually added thereinto and further, 4.2 g (0.10 mol) of caustic soda was added thereinto. By generating the heat of reaction, the temperature of reaction solution was raised to about 60° C. and the reaction was continued at the temperature for 3 hours. Thereafter, the reaction mixture was cooled and filtered to remove the sodium chloride generated as the byproduct. The obtained filtrate was distilled under reduced pressure to recover the solvent. Therefore, 18.3 g (0.05 mol) of 4,6-dichloro-2-diallylamino-1,3,5-triazine was obtained.

Then, after 4.2 g (0.10 mol) of caustic soda and 18.3 g (0.05 mol) of the above obtained 4,6-dichloro-2-diallylamino-1,3,5-triazine were added and dissolved into 140 g of 1,4-dioxane, 5.9 g (0.10 mol) of allyl alcohol was gradually added. By generating the heat of reaction, the temperature of reaction solution was raised to about 60° C. and the reaction was continued at the temperature for 6 hours. Thereafter, the reaction mixture was cooled and filtered to remove the sodium chloride generated as the byproduct (forming by reaction of 4,6-dichloro-2-diallylamino-1,3,5-triazine as the reaction material with the caustic soda). The obtained filtrate was distilled under reduced pressure to recover the solvent. The obtained residue was diluted with ethyl acetate, washed with 5% by weight of aqueous hydrochloric acid solution, washed with water and thereafter, dried by anhydrous magnesium sulfate and filtered. The obtained filtrate is distilled under reduced pressure to recover the ethyl acetate contained therein. Further, the residue was distilled (distillation temperature: 155° C., degree of vacuum: 0.5 Torr) to obtain 11.6 g (0.04 mol) of liquid 4,6-bis(allyloxy)-2-diallylamino-1,3,5-triazine (LC purity: 99%, yield: 40%). The identification and "LC purity" of compound were carried out by the same manner as described in Synthesis Example 1.

The NMR measurement results of the above triazine derivative were δ: 5.7-6.2 ppm, 4H(m), 5.05-5.5 ppm, 7H(m), 4.85 ppm, 4H(d), 4.3 ppm, 4H (d), and GC-MS measurement was (CI)(M+1): 289.

Examples 1 to 3 and Comparative Example 1

By use of an open roll, the respective components shown in Table 3 were kneaded to a fluorine rubber in the amount ratio shown in Table 3 at 90° C. The obtained composition as the material was subject to heat-press cross-linking (primary cross-linking) under the conditions shown in Table 3 and then, the secondary cross-linking was carried out under the conditions shown in Table 4. The mechanical properties of obtained respective cross-linked products were evaluated. The results are shown in Table 4. In addition, evaluation methods used in the following Examples are shown as follows.

TABLE 3

|  | Example 1 | Example 2 | Example 3 | Comp. Example 1 |
|---|---|---|---|---|
| Conditions for primary cross-linking | 160° C. × 25 min | 170° C. × 20 min | 170° C. × 15 min | 160° C. × 10 min |
| Fluorine rubber[1] (parts by weight) | 100 | 100 | 100 | 100 |
| MT carbon[2] (parts by weight) | 20 | 20 | 20 | 20 |
| Organic peroxide[3] (parts by weight) | 3.75 | 3.75 | 3.75 | 3.75 |
| Cross-linking agent-1[4] (parts by weight) | 4 | — | 3 | — |
| Cross-linking agent-2[5] (parts by weight) | — | 4 | — | — |
| Cross-linking agent-3[6] (parts by weight) | — | — | 1 | 4 |

[1]"DAI-EL G-902" manufactured by Daikin Industries, Ltd.
[2]"Thermax MT N990" manufactured by Carbons Inc.
[3]2,5-dimethyl-2,5-(t-butylperoxy)hexane manufactured by NOF Corporation
[4]4,6-bis(diallylamino)-2-allyloxy-1,3,5-triazine obtained in Synthesis Example 1
[5]4,6-bis(allyloxy)-2-diallylamino-1,3,5-triazine obtained in Synthesis Example 2
[6]Triallyl isocyanate manufactured by Nippon Kasei Chemical Company Limited <Evaluation Methods>
(1) The respective properties of tensile strength (MPa), 100% tensile stress (MPa) and elongation (%) were measured according to ASTM D 638. The hardness (Shore A) was measured according to JIS K 6253.
(2) Thermal degradation test was performed by using a test piece punched out to the form No. 3 dumbbell-shaped as defined JIS K 6251 and treating in a gear oven at 250° C. for 70 hours. As the gear oven, "Gear heat aging testing machine" (type ACR-60A) manufactured by Toyo Seiki Seisaku-Sho, Ltd. was used.

TABLE 4

|  | Example 1 | Example 2 | Example 3 | Comp. Example 1 |
|---|---|---|---|---|
| Conditions for secondary cross-linking | 180° C. × 4 hr | 180° C. × 4 hr | 180° C. × 4 hr | 180° C. × 4 hr |
| Ordinary state properties |  |  |  |  |
| Tensile strength (MPa) | 15.1 | 20.6 | 17.5 | 23.3 |
| 100% tensile stress (MPa) | 4.1 | 3.8 | 3.8 | 3.9 |

TABLE 4-continued

|  | Example 1 | Example 2 | Example 3 | Comp. Example 1 |
|---|---|---|---|---|
| Elongation (%) | 340 | 350 | 310 | 310 |
| Hardness (Shore A) | 78 | 71 | 72 | 70 |
| Ratio of difference after the thermal degradation test |  |  |  |  |
| Ratio of difference of tensile strength (%) | −35 | −33 | −32 | −66 |
| Ratio of difference of elongation (%) | +18 | +35 | +65 | — |
| Ratio of difference of hardness (%) | 0 | +2 | +6 | +1 |

Examples 4-5 and Comparative Example 2

By use of an open roll, the respective components shown in Table 5 were kneaded to an ethylene-vinyl acetate copolymer (EVA) in the amount ratio shown in Table 5. The obtained composition was subject to heat-press cross-linking (primary cross-linking) at 150° C. to obtain a sheet having 1 mm thickness.

When kneading above, by using a Curelastometer, the torque of composition (150° C.) was read the value over 15 minutes to measure the cross-linking rate of the composition. The intermediate value of maximum torque value and minimum torque value was "torque when cross-linking rate is 50%" and the time requiring therefor is "time when the cross-linking percentage is reached to 50%". Then, the value of 30% of the difference between the maximum torque value and minimum torque value was "torque when cross-linking rate is 30%" and the time requiring therefor is "time when the cross-linking percentage is reached to 30%". The evaluation results are shown in Table 6.

TABLE 5

| Compounding (parts by weight) | Example 4 | Example 5 | Comp. Example 2 |
|---|---|---|---|
| EVA[1] | 100 | 100 | 100 |
| Organic peroxide[2] | 1.3 | 1.3 | 1.3 |
| Cross-linking agent-1[3] | 0.1 | 0.2 | — |
| Cross-linking agent-3[4] | 1.8 | 1.8 | 2.0 |
| Silane coupling agent[5] | 0.5 | 0.5 | 0.5 |
| Ultra violet absorber[6] | 0.2 | 0.2 | 0.2 |

[1]Vinyl acetate content: 26% by weight
[2]2,5-dimethyl-2,5-(t-butylperoxy)hexane (manufactured by NOF Corporation)
[3]4,6-bis(diallylamino)-2-allyloxy-1,3,5-triazine obtained in Synthesis Example 1
[4]Triallyl isocyanurate (manufactured by Nippon Kasei Chemical Co., Ltd.)
[5]γ-methacryloxy propyltrimethoxy silane
[6]2-hydroxy-4-n-benzophenone octoxyphenyl

TABLE 6

| Evaluation results | Example 4 | Example 5 | Comp. Example 2 |
|---|---|---|---|
| Torque when cross-linking rate is 50% (dNm) | 3.0 | 3.0 | 3.0 |
| Time when the cross-linking percentage is reached to 50 (min) | 7.2 | 7.4 | 7.7 |
| Torque when cross-linking rate is 30% (dNm) | 1.9 | 1.9 | 1.9 |
| Time when the cross-linking percentage is reached to 30% (min) | 6.3 | 5.9 | 6.6 |

<Measurement of Heat-Resistant Durability>

The composition shown in Table 7 was kneaded and heat-pressed at 150° C. for 20 minutes to obtain a sheet-like molded product of ethylene-vinyl acetate copolymer. The composition of Comparative Example 2 in Table 7 is the same composition shown in Table 5 as Comparative Example 2. The respective components shown in Table 7 are the same components shown in Table 5 except for Cross-linking agent-2.

TABLE 7

| Compounding (parts by weight) | Example 4 | Example 5 | Comp. Example 2 |
|---|---|---|---|
| EVA | 100 | 100 | 100 |
| Organic peroxide | 1.3 | 1.3 | 1.3 |
| Cross-linking agent-1 | 0.1 | 0.2 | — |
| Cross-linking agent-2[(7)] | 0.1 | 0.2 | — |
| Cross-linking agent-3 | 1.8 | 1.8 | 2.0 |
| Silane coupling agent | 0.5 | 0.5 | 0.5 |
| Ultra violet absorber | 0.2 | 0.2 | 0.2 |

[(7)]4,6-bis(allyloxy)-2-diallylamino-1,3,5-triazine obtained in Synthesis Example 2

Then, a strip sheet of ethylene vinyl acetate copolymer (33 mm width and 110 mm length) was cut out from the molded product and used as a test piece for the heat-resistance durability. The obtained test piece was kept in a gear oven at 90° C. for 500 hours, 700 hours and 900 hours. To the test pieces after respective keeping times, the following physical properties of (1) to (3) were evaluated. The evaluation results are shown in Tables 8 to 10.

(1) 100% Modulus:

The test piece was molded to a dumbbell-shaped test piece (tensile form No. 3, JIS K 6251) to prepare a tensile test specimen. Then, the tensile stress test of test specimen was conducted by using an Autograph (AGS-10kNG type, manufactured by Shimadzu Corporation) and the tensile strength (MPa) when the elongation between the marked lines became a 100% increase at the start of the test was measured and was referred as 100% modulus. The measurement was conducted with a tensile speed of 200 mm/min.

(2) Degree of Swelling:

A small strip (10 mm width and 20 mm length) was cut out from the molded product to prepare a test specimen for the measurement of degree of swelling. Then, the prepared test specimen for the measurement of degree of swelling was immersed into 30 mL of tetrahydrofuran at 25° C. for 24 hours. By using the weight change of test specimen before and after the immersing and the following formula, the degree of swelling of test specimen was determined.

Degree of swelling (−)=(weight of test specimen after the swelling test (g)−weight of test specimen before the swelling test (g))/(weight of test specimen before the swelling test (g))  [Formula 1]

(3) Total Light Transmittance:

By using a haze meter (NDH-2000 type, manufactured by NIPPON DENSHOKU INDUSTRUIES CO., LTD.), the total light transmittance of test specimen was measured at three portions and the average value thereof was calculated.

TABLE 8

(100% modulus (unit: MPa))

| Time (hour) | Example 6 | Example 7 | Comp. Example 2 |
|---|---|---|---|
| 0 | 3.65 | 3.47 | 3.58 |
| 500 | 3.76 | 3.57 | 3.51 |
| 700 | 3.87 | 3.28 | 2.99 |
| 900 | 3.69 | 2.76 | 2.21 |

TABLE 9

(Degree of swelling (no unit))

| Time (hour) | Example 6 | Example 7 | Comp. Example 2 |
|---|---|---|---|
| 0 | 3.99 | 4.08 | 4.00 |
| 500 | 4.05 | 5.21 | 6.02 |
| 700 | 4.20 | 6.28 | 6.85 |
| 900 | 4.60 | 6.40 | * |

(* The test specimen was dissolved into tetrahydrofuran)

TABLE 10

(Total light transmittance (unit: %))

| Time (hour) | Example 6 | Example 7 | Comp. Example 2 |
|---|---|---|---|
| 0 | 91.94 | 91.33 | 91.59 |
| 500 | 90.44 | 89.26 | 87.40 |
| 700 | 90.18 | 87.08 | 84.82 |
| 900 | 90.35 | 86.38 | 84.53 |

INDUSTRIAL APPLICABILITY

The molded product of cross-linkable elastomer composition according to the present invention using the ethylene-vinyl acetate copolymer as the polyolefin substituted is useful for applications such as: packaging materials for various materials such as foods, pharmaceuticals, industrial chemicals and agricultural chemicals, various adhesive films sealing films for solar cells, as well as useful in fields of hemodialysis, plasma component separation, desalting of protein solutions, fractionation, condensation, condensation of fruit juice and wastewater treatment. In addition, The molded product of cross-linkable elastomer composition according to the present invention using the fluorine rubber is useful for applications such as automotive oil seals, O-rings, seals, hoses, electric wires, semiconductors or the like.

The invention claimed is:

1. A triazine derivative represented by formula (I)

wherein (a) Y and X represent a diallylamino group or (b) one of Y or X represents a diallylamino group and the other of X or Y represents a mono-allylamino group, allyloxy group or methallyloxy group; and Z represents an allyloxy group or methallyloxy group.

2. A cross-linking agent comprising the triazine derivative represented by formula (I) as defined in claim 1 or prepolymer thereof.

3. A cross-linkable polymer composition comprising a cross-linkable polymer and the triazine derivative represented by formula (I) as defined in claim 1 or prepolymer thereof blended thereto, the blending ratio of the triazine derivative or prepolymer thereof being 0.05 to 15 parts by weight based on 100 parts by weight of cross-linkable polymer.

4. A cross-linkable polymer composition according to claim 3, wherein the cross-linkable polymer is a cross-linkable elastomer.

5. A cross-linkable polymer composition according to claim 4, wherein the cross-linkable elastomer is a substituted polyolefin or a fluorine rubber.

6. A cross-linkable polymer composition according to claim 5, wherein the substituted polyolefin is an ethylene-vinyl acetate copolymer.

7. A process for producing a polymer molded product comprising curing the cross-linkable polymer composition as defined in claim 3.

8. A process according to claim 7, wherein the cross-linkable polymer is a cross-linkable elastomer.

9. A process according to claim 8, wherein the cross-linkable elastomer is a substituted polyolefin or a fluorine rubber.

10. A process according to claim 9, wherein the substituted polyolefin is an ethylene-vinyl acetate copolymer.

11. A polymer molded product cured by the action of a crosslinking agent, produced using a cross-linkable polymer and the triazine derivative represented by the above formula (I) as defined in claim 1 or prepolymer thereof as a cross-linking agent.

12. A polymer molded product according to claim 11, wherein the cross-linkable polymer is a cross-linkable elastomer.

13. A polymer molded product according to claim 12, wherein the cross-linkable elastomer is a substituted polyolefin or a fluorine rubber.

14. A polymer molded product according to claim 13, wherein the substituted polyolefin is an ethylene-vinyl acetate copolymer.

15. A polymer molded product according to claim 11, wherein a rate of tensile strength change (MPa) measured according to ASTM D 638 before and after the thermal degradation tests under the following conditions: a ratio of the difference of the tensile strengths between after and before the test to the tensile strength before the test is −55% to 0%.

* * * * *